United States Patent
Dumas et al.

(10) Patent No.: US 11,384,342 B2
(45) Date of Patent: Jul. 12, 2022

(54) SELECTION MARKER FOR CELL TRANSFECTION AND PROTEIN PRODUCTION

(71) Applicant: Sanofi, Paris (FR)

(72) Inventors: Bruno Dumas, Paris (FR); Nabil Lounis, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 16/727,212

(22) Filed: Dec. 26, 2019

(65) Prior Publication Data

US 2020/0199543 A1    Jun. 25, 2020

Related U.S. Application Data

(63) Continuation of application No. 15/520,840, filed as application No. PCT/EP2015/074550 on Oct. 22, 2015, now Pat. No. 10,557,125.

(30) Foreign Application Priority Data

Oct. 23, 2014 (EP) .................................. 14306689

(51) Int. Cl.
| | |
|---|---|
| C12N 9/02 | (2006.01) |
| C12N 1/20 | (2006.01) |
| C12N 15/00 | (2006.01) |
| C12P 21/04 | (2006.01) |
| C12N 15/85 | (2006.01) |
| C12N 15/65 | (2006.01) |
| C12P 21/00 | (2006.01) |
| C12N 15/09 | (2006.01) |
| A61K 38/00 | (2006.01) |

(52) U.S. Cl.
CPC ............. *C12N 9/001* (2013.01); *C12N 15/09* (2013.01); *C12N 15/65* (2013.01); *C12N 15/85* (2013.01); *C12P 21/00* (2013.01); *C12Y 103/05002* (2013.01); *A61K 38/00* (2013.01)

(58) Field of Classification Search
CPC ................................ C12N 9/001; C12P 21/00
See application file for complete search history.

(56) References Cited

U.S. PATENT DOCUMENTS

| | | | |
|---|---|---|---|
| 9,334,489 B2 | 5/2016 | Devaud et al. | |
| 2003/0166201 A1 | 9/2003 | Jensen | |

FOREIGN PATENT DOCUMENTS

| | | |
|---|---|---|
| KR | 100267720 | 7/2000 |
| WO | WO 1989/01036 | 2/1989 |

(Continued)

OTHER PUBLICATIONS

Xu. G3HAH3_CRIGR. UnitProtKB Database. 2013.*

(Continued)

*Primary Examiner* — Yong D Pak
(74) *Attorney, Agent, or Firm* — McDonnell Boehnen Hulbert & Bergthoff LLP

(57) ABSTRACT

The present invention is within the field of industrial protein production. The invention provides a novel expression system using dehydroorotate dehydrogenase (DHODH) as a selection marker in combination with leflunomide or a metabolite thereof, notably for use in mammalian cell lines. Expression vectors encoding DHODH, cell lines comprising said vectors and methods of producing recombinant proteins are also provided.

5 Claims, 5 Drawing Sheets

Specification includes a Sequence Listing.

(56) References Cited

FOREIGN PATENT DOCUMENTS

| WO | WO 2009/133379 | 11/2009 | | |
|----|----|----|----|----|
| WO | WO 2010/132341 | 11/2010 | | |
| WO | WO-2012109329 A2 | * | 8/2012 | ............ A61K 31/122 |
| WO | WO 2013/186371 | 12/2013 | | |
| WO | WO 2014/100073 | 6/2014 | | |

OTHER PUBLICATIONS

GenBank: ERE78904.1—dihydroorotate dehydrogenase (quinone) [Cricetulus griseus] Mar. 22, 2015; 2 pages.
Bader et al: "Expression, Purification, and Characterization of Histidine-Tagged Rat and Human Flavoenzyme Dihydroorotate Dehydrogenase", Protein Expression and Purification, Aug. 1, 1998 vol. 13, No. 3, pp. 414-422, Academic Press.
Benoist and Chambon "In vivo sequence requirements of the SV40 early promoter region." Nature. 1981, 290:304-10, Springer Nature.
Chatellard et al: "The IE2 Promoter/Enhancer Region From Mouse CMV Provides High Levels of Therapeutic Protein Expression in Mammalian Cells." Biotechnol Bioeng. 2007, 96:106-17, Wiley.
Ganesan et al: "Yeast Dihydroorotate Dehydrogenase as a New Selectable Marker for Plasmodium falciparum Transfection." Molecular and Biochemical Parasitology. 2011, 177: 29-34, Elsevier.
Moreau et al: "The SV40 72 base repair repeat has a striking effect on gene expression both in SV40 and other chimeric recombinants." Nucleic Acids Res. 1981 9:6047-68, Oxford University Press.
Needleman and Wunsch, "A general method applicable to the search for similarities in the amino acid sequence of two proteins." J. Mol. Biol 1970 48:443-453, Elsevier.
Neidhardt et al: "Human Dihydroorotate Dehydrogenase Production in *E. coli* 183 Expression and Characterization of *E. coli*-produced Soluble, Functional Human Dihydroorotate Dehydrogenase: a Potential Target for Immunosuppression." J. Molec. Microbiol. Biotechnol, Jan. 1, 1999, pp. 183-188.
Raab et al: "The GeneOptimizer Algorithm: using a sliding window approach to cope with the vast sequence space in multiparameter DNA sequence optimization." Syst Synth Biol. 2010 4:215-25, Springer Science+Business Media.
Teschendorf et al: "Comparison of the EF-1 alpha and the CMV promoter for engineering stable tumor cell lines using recombinant adeno-associated virus." Anticancer Res., 2002, 22:3325-30, International Institute of Anticancer Research.
Wagner et al: "An integrated strategy for efficient vector construction and multi-gene expression in Plasmodium falciparum." Malaria Journal, Oct. 26, 2013, vol. 12, No. 1, pp. 373, BioMed Central.
International Preliminary Report on Patentability, dated Apr. 25, 2017, European Patent Office, issued in International Patent Application No. PCT/EP2015/074550.
International Search Report and Written Opinion, dated Jan. 26, 2016, European Patent Office, issued in International Patent Application No. PCT/EP2015/074550.
Erra (Biaryl analogues of teriflunomide as potent DHODH inhibitors. Bioorg Med Chem Lett. Dec. 15, 2011;21 (24):7268-72. doi: 10.1016/j.bmcl.2011.10.052. Epub Oct. 20, 2011.
Q02127. UniProtKB. 2013.
GenBank: NP_001352.2 "dihydroorotate dehydrogenase (quinone), mitochondrial [*Homo sapiens*]" dated Jun. 25, 2018; accessed Oct. 30, 2018, three pages.
Gen Bank: XP_007634457.1 "Predicted: dihydroorotate dehydrogenase (quinone), mitochondrial isoform X1 [Cricetulus griseus]" dated May 27, 2016; accessed Oct. 30, 2018, two pages.
Kabat, et al., Sequences of Proteins of Immunological Interest, Fifth Edition, U.S. Department of Heath and Human Services, National Institutes of Health, NIH Publication No. 91-3242; 83 pages (1991).
Palmer, A.M., "Teriflunomide, an inhibitor of dihydroorotate dehydrogenase for the potential oral treatment of multiple sclerosis", Current Opinion in Investigational Drugs, 11(11), pp. 1313-1323, Nov. 1, 2010 (Nov. 1, 2010).

* cited by examiner

SEQUENCE LISTING

<160> NUMBER OF SEQ ID NOS: 4

<210> SEQ ID NO 1
<211> LENGTH: 1188

```
<212> TYPE: DNA
<213> ORGANISM: Cricetus cricetus

<400> SEQUENCE: 1
atggcttggc ggcagatgcg aagagagcc ctggacgccg ctatcatcct gggaggcgga      60
ggcctgctgt tcacctctta cctgacagcc accggcgacg accacttcta cgccgagtac     120
ctgatgcctg ccctgcagag actgctggac ctgagtctg cccaccggct ggccatcaga     180
ttcacctccc tgggcctgct gcccagagcc accttccagg actccgacat gctggaagtg     240
cgggtgctgg gccacaagtt cagaaacccc gtgggaatcg ccgctggctt cgacaagcac     300
ggcgaggctg tggacggcct gtacaagctg ggcttcggct cgtggaagt gggctccgtg      360 acaccccagc cccaggaagg caaccccaga cctagagtgt tccggctgcc tgaggaccag     420
gccgtgatca cagatacgg cttcaactcc cacggcctgt ccgtggtgga caccggctg      480 agagccagac agcagaagca gaacaagctg accgccgacg gcctgcccct gggcatcaat     540
ctgggcaaga acaagacctc cgaggacgct gccgccgact acgtgaagg cgtgcgagtg      600 ctgggacctc tggccgatta cctggtcgtg aacgtgtcct ccccaacac cgctggcctg      660 agaagcctgc agggaaaggc cgagctgaga aggctgctgg ccaaggtgct gcaggaacgg     720
gacgctctga agggcgccca gaaacctgcc gtgctcgtga agatcgcccc tgacctgacc     780
gcccaggaca agaggatat cgcctccgtg gccagagagc tgggcatcga cggactgatc     840
gtgaccaaca ccaccgtgtc tcggcctacc ggactgcagg gcgctctgag atctgagatg     900
ggcggcctgt ctggcaagcc tctgagggac ctgtccaccc agaccatcag agagatgtac     960
accctgaccc agggccggat ccccatcatt ggagtgggcg gagtgtcctc tggccaggac    1020
gccctggaaa agatccaggc tggcgcctct ctggtgcagc tgtataccgc cctgaccttt    1080
ctgggccctc ccgtggtggt gcgagtgaag agagaactgg aagccctgct gaaagagcgg    1140
ggcttcaaca ccgtgaccga ggccatcggc gctgaccaca aagatga                    1188

<210> SEQ ID NO 2
<211> LENGTH: 395
<212> TYPE: PRT
<213> ORGANISM: Cricetus cricetus

<400> SEQUENCE: 2

Met Ala Trp Arg Gln Met Arg Lys Arg Ala Leu Asp Ala Ala Ile Ile
1               5                   10                  15

Leu Gly Gly Gly Gly Leu Leu Phe Thr Ser Tyr Leu Thr Ala Thr Gly
            20                  25                  30

Asp Asp His Phe Tyr Ala Glu Tyr Leu Met Pro Ala Leu Gln Arg Leu
        35                  40                  45

Leu Asp Pro Glu Ser Ala His Arg Leu Ala Ile Arg Phe Thr Ser Leu
    50                  55                  60

Gly Leu Leu Pro Arg Ala Thr Phe Gln Asp Ser Asp Met Leu Glu Val
65                  70                  75                  80

Arg Val Leu Gly His Lys Phe Arg Asn Pro Val Gly Ile Ala Ala Gly
                85                  90                  95

Phe Asp Lys His Gly Glu Ala Val Asp Gly Leu Tyr Lys Leu Gly Phe
            100                 105                 110

Gly Phe Val Glu Val Gly Ser Val Thr Pro Gln Pro Gln Glu Gly Asn
        115                 120                 125

Pro Arg Pro Arg Val Phe Arg Leu Pro Glu Asp Gln Ala Val Ile Asn
    130                 135                 140
```

Arg Tyr Gly Phe Asn Ser His Gly Leu Ser Val Val Glu His Arg Leu
145                 150                 155                 160

Arg Ala Arg Gln Gln Lys Gln Asn Lys Leu Thr Ala Asp Gly Leu Pro
                165                 170                 175

Leu Gly Ile Asn Leu Gly Lys Asn Lys Thr Ser Glu Asp Ala Ala Ala
            180                 185                 190

Asp Tyr Val Glu Gly Val Arg Val Leu Gly Pro Leu Ala Asp Tyr Leu
        195                 200                 205

Val Val Asn Val Ser Ser Pro Asn Thr Ala Gly Leu Arg Ser Leu Gln
210                 215                 220

Gly Lys Ala Glu Leu Arg Arg Leu Leu Ala Lys Val Leu Gln Glu Arg
225                 230                 235                 240

Asp Ala Leu Lys Gly Ala Gln Lys Pro Ala Val Leu Val Lys Ile Ala
                245                 250                 255

Pro Asp Leu Thr Ala Gln Asp Lys Glu Asp Ile Ala Ser Val Ala Arg
            260                 265                 270

Glu Leu Gly Ile Asp Gly Leu Ile Val Thr Asn Thr Thr Val Ser Arg
        275                 280                 285

Pro Thr Gly Leu Gln Gly Ala Leu Arg Ser Glu Met Gly Gly Leu Ser
290                 295                 300

Gly Lys Pro Leu Arg Asp Leu Ser Thr Gln Thr Ile Arg Glu Met Tyr
305                 310                 315                 320

Thr Leu Thr Gln Gly Arg Ile Pro Ile Ile Gly Val Gly Gly Val Ser
                325                 330                 335

Ser Gly Gln Asp Ala Leu Glu Lys Ile Gln Ala Gly Ala Ser Leu Val
            340                 345                 350

Gln Leu Tyr Thr Ala Leu Thr Phe Leu Gly Pro Pro Val Val Val Arg
        355                 360                 365

Val Lys Arg Glu Leu Glu Ala Leu Leu Lys Glu Arg Gly Phe Asn Thr
370                 375                 380

Val Thr Glu Ala Ile Gly Ala Asp His Arg Arg
385                 390                 395

<210> SEQ ID NO 3
<211> LENGTH: 1188
<212> TYPE: DNA
<213> ORGANISM: Homo sapiens

<400> SEQUENCE: 3
atggcttggc ggcacctgaa gaagagggcc caggacgccg tgatcatcct ggagggcgga      60
ggcctgctgt tcgcctctta cctgatggct accggcgacg agcggttcta cgccgagcat     120
ctgatgccca cactgcaggg cctgctggac cctgagtctg cccatagact ggccgtgcgg     180
ttcacctccc tgggactgct gcctagagcc cggttccagg actccgacat gctggaagtg     240
cgggtgctgg ccacaagtt cagaaacccc gtgggaatcg ccgctggctt cgacaagcac     300
ggcgaggctg tggacggcct gtacaagatg ggcttcggct tcgtggaaat cggctccgtg     360 accccccaagc cccaggaagg caaccccaga cctcgggtgt tcagactgcc tgaggaccag     420
gctgtgatca acagatacgg cttcaactcc cacggcctgt ccgtggtgga acaccggctg     480
agagccagac agcagaagca ggccaagctg accgaggatg cctgcctct gggagtgaac     540 ctgggcaaga acaagacctc cgtggacgcc gccgaggatt acgctgaagg cgtgcgagtg     600
ctgggacccc tggctgatta cctggtcgtg aacgtgtcct cccccaacac cgctggcctg     660

```
agatctctgc agggcaaggc cgagctgcgg agactgctga caaaggtgct gcaggaacgc    720
gacggcctgc ggagagtgca tagacctgcc gtgctcgtga agatcgcccc cgacctgacc    780
agccaggaca agaggatat cgcctccgtc gtgaaagagc tgggcatcga cggactgatc    840
gtgaccaaca ccaccgtgtc taggcctgcc ggactgcagg gggctctgag atctgaaacc    900
ggcggactgt ccggcaagcc tctgagggat ctgtccaccc agaccatcag agagatgtac    960
gccctgaccc agggccgggt gccaatcatt ggagtgggcg agtgtcctc cggccaggat   1020 gccctggaaa agatcagagc cggcgcttcc ctggtgcagc tgtacaccgc tctgaccttt   1080 tgggccctc ccgtcgtggg caaagtgaag agagagctgg aagccctgct gaaagagcag   1140
ggatttggcg gcgtgaccga tgccatcggc gctgaccaca aagatga                1188
```

<210> SEQ ID NO 4
<211> LENGTH: 395
<212> TYPE: PRT
<213> ORGANISM: Homo sapiens

<400> SEQUENCE: 4

```
Met Ala Trp Arg His Leu Lys Lys Arg Ala Gln Asp Ala Val Ile Ile
1               5                   10                  15

Leu Gly Gly Gly Gly Leu Leu Phe Ala Ser Tyr Leu Met Ala Thr Gly
            20                  25                  30

Asp Glu Arg Phe Tyr Ala Glu His Leu Met Pro Thr Leu Gln Gly Leu
        35                  40                  45

Leu Asp Pro Glu Ser Ala His Arg Leu Ala Val Arg Phe Thr Ser Leu
    50                  55                  60

Gly Leu Leu Pro Arg Ala Arg Phe Gln Asp Ser Asp Met Leu Glu Val
65                  70                  75                  80

Arg Val Leu Gly His Lys Phe Arg Asn Pro Val Gly Ile Ala Ala Gly
                85                  90                  95

Phe Asp Lys His Gly Glu Ala Val Asp Gly Leu Tyr Lys Met Gly Phe
            100                 105                 110

Gly Phe Val Glu Ile Gly Ser Val Thr Pro Lys Pro Gln Glu Gly Asn
        115                 120                 125

Pro Arg Pro Arg Val Phe Arg Leu Pro Glu Asp Gln Ala Val Ile Asn
    130                 135                 140

Arg Tyr Gly Phe Asn Ser His Gly Leu Ser Val Val Glu His Arg Leu
145                 150                 155                 160

Arg Ala Arg Gln Gln Lys Gln Ala Lys Leu Thr Glu Asp Gly Leu Pro
                165                 170                 175

Leu Gly Val Asn Leu Gly Lys Asn Lys Thr Ser Val Asp Ala Ala Glu
            180                 185                 190

Asp Tyr Ala Glu Gly Val Arg Val Leu Gly Pro Leu Ala Asp Tyr Leu
        195                 200                 205

Val Val Asn Val Ser Ser Pro Asn Thr Ala Gly Leu Arg Ser Leu Gln
    210                 215                 220

Gly Lys Ala Glu Leu Arg Arg Leu Leu Thr Lys Val Leu Gln Glu Arg
225                 230                 235                 240

Asp Gly Leu Arg Arg Val His Arg Pro Ala Val Leu Val Lys Ile Ala
                245                 250                 255

Pro Asp Leu Thr Ser Gln Asp Lys Glu Asp Ile Ala Ser Val Val Lys
            260                 265                 270

Glu Leu Gly Ile Asp Gly Leu Ile Val Thr Asn Thr Thr Val Ser Arg
        275                 280                 285
```

```
Pro Ala Gly Leu Gln Gly Ala Leu Arg Ser Glu Thr Gly Gly Leu Ser
    290                 295                 300

Gly Lys Pro Leu Arg Asp Leu Ser Thr Gln Thr Ile Arg Glu Met Tyr
305                 310                 315                 320

Ala Leu Thr Gln Gly Arg Val Pro Ile Ile Gly Val Gly Gly Val Ser
                325                 330                 335

Ser Gly Gln Asp Ala Leu Glu Lys Ile Arg Ala Gly Ala Ser Leu Val
                340                 345                 350

Gln Leu Tyr Thr Ala Leu Thr Phe Trp Gly Pro Pro Val Val Gly Lys
        355                 360                 365

Val Lys Arg Glu Leu Glu Ala Leu Leu Lys Glu Gln Gly Phe Gly Gly
    370                 375                 380

Val Thr Asp Ala Ile Gly Ala Asp His Arg Arg
385                 390                 395
```

SELECTION MARKER FOR CELL TRANSFECTION AND PROTEIN PRODUCTION This application is a continuation of U.S. patent application Ser. No. 15/520,840, filed Apr. 20, 2017, which is a is a national stage application under 35 U.S.C. § 371 of International Application No. PCT/EP2015/074550, filed Oct. 22, 2015, which claims the benefit of European Application No. EP 14306689.2, filed Oct. 23, 2014, the disclosure of which are explicitly incorporated herein in their entirety by reference.

FIELD OF THE INVENTION

The present invention is within the field of industrial protein production. The invention provides a novel expression system using dihydroorotate dehydrogenase (DHODH) as a selection marker in combination with a DHODH inhibitor, in particular with teriflunomide, notably for use in mammalian cell lines. Expression vectors encoding DHODH, cell lines comprising said vectors and methods of producing recombinant proteins are also provided.

BACKGROUND OF THE INVENTION

Producing recombinant proteins on an industrial scale requires isolation of clones producing high amounts of recombinant proteins. Introducing heterologous genes into animal host cells and screening for expression of the added genes is a lengthy and complicated process. The process involves the transfection and the selection of clones with stable long-term expression, and the screening for clones having high expression rates for the corresponding recombinant protein.

When generating clones expressing a recombinant protein from expression vectors, host cells are usually transfected with a DNA vector encoding both the protein of interest and the selection marker on the same vector. Such an expression vector thus comprises a selectable marker allowing the selection of clones in which the expression vector is present. Such a selectable marker may also lead to a co-amplification of transfected DNA, thereby allowing the isolation of high-producer clones.

Most selectable markers are either a protein conferring resistance to an antibiotic or other toxic substance or a protein essential to cell survival. Several such selectable markers are known in the art, including e.g. G418, hygromycin, puromycin, zeomycin, dihydrofolate reductase (DHFR), glutamine synthetase (GS) and hypoxanthine-guanine phosphoribosyltransferase (HPRT). In particular, GS is widely used as a selectable marker in the field of industrial recombinant protein production in eukaryotic cells. The GS gene permits the synthesis of glutamine, essential for cell growth, and is inhibited by MSX (L-methionine sulfoximine). In the presence of MSX, only cells expressing higher amount of GS do survive. After appropriate screening it is possible to select cells producing the exogenous proteins.

The development of additional expression systems allowing the isolation of a high number of clones expressing the recombinant protein, at least some of which express the protein at a high level, will extend the options available when producing recombinant proteins and increase the possibilities for identifying high-expressing clones suitable for use in protein production in a large scale.

SUMMARY OF THE INVENTION

The inventors have developed a new expression system based on the use of dihydroorotate dehydrogenase (DHODH) as a selectable marker. DHODH is an enzyme required for pyrimidine synthesis. Compounds which inhibit DHODH therefore inhibit DNA synthesis and hence cell proliferation. The inventors speculated that overexpression of wild-type DHODH in cells can confer resistance to DHODH inhibitors, based on the principle that toxicity of a compound can be relieved by overexpression of its target. They developed an antibody expression vector encoding DHODH for use in combination with DHODH inhibitors including leflunomide (IUPAC name: 5-methyl-N-[4-(trifluoromethyl) phenyl]-isoxazole-4-carboxamide) and teriflunomide (IUPAC name: (2Z)-2-cyano-3-hydroxy-N-[4-(trifluoromethyl)phenyl]but-2-enamide). They surprisingly found that isolation of clones producing antibodies was more efficient when the DHODH inhibitor is teriflunomide. They showed that the use of an expression system comprising said vector in CHO (stands for Chinese Hamster Ovary) cells cultured with teriflunomide enabled the isolation of clones producing antibodies at levels comparable to the standard GS marker.

This is the first time that DHODH has been used as a selectable marker in the context of production of recombinant proteins in cell culture.

US2003/0166201 describes the use of inhibitor-resistant or altered DHODH which is not inhibited by the selection agent as a selectable marker. However, US2003/0166201 does not describe DHODH as a marker for the use in production of recombinant proteins. Moreover, US2003/0166201 does not disclose the use of a wild-type DHODH or altered DHODH which is inhibited by the selection agent, but is limited to use of DHODH which is not inhibited by the selection agent.

Ganesan et al (2011), Molecular and Biochemical Parasitology 177: 29-34 disclose the use of yeast DHODH as a selectable marker for transfection of *P. falciparum*, using atovaquone and the *P. falciparum*-specific inhibitors DSM1 and DSM74 as selection agent. However, Ganesan et al do not describe DHODH as a marker for use in production of recombinant proteins. Moreover, their results are specific to transformation of *P. falciparum* genes using the yeast DHODH.

In summary, the inventors have shown for the first time that DHODH is an effective selectable marker for obtaining clones producing recombinant proteins. Moreover, they have also demonstrated that a wild-type DHODH which is sensitive to the selection agent used may be used for this purpose.

Thus, the present invention provides an expression vector comprising a nucleotide sequence coding for a mammalian dihydroorotate dehydrogenase (DHODH) and at least one expression cassette for expressing a recombinant protein. Said DHODH may be as defined below, and may in particular comprise the sequence of SEQ ID NO: 2 or SEQ ID NO: 4 or a variant thereof having DHODH activity. In one embodiment, said variant is sensitive to inhibitors of DHODH activity as described herein, preferably sensitive to teriflunomide.

In some embodiments, the triplet codons of said sequence coding for DHODH have been biased for expression in specific cells, for example CHO cells or human cells. In some embodiments, said nucleotide sequence comprises the sequence of SEQ ID NO: 1 or the sequence of SEQ ID NO: 3.

In some embodiments, said recombinant protein is an antibody (e.g. a monoclonal antibody), a chimiokine, a lymphokine, a hormone (e.g. insulin), an immunogenic protein for inducing an antibody response or an enzyme for enzyme replacement therapy or for industrial use. Where said protein is an antibody, said vector may comprises a first expression cassette suitable for cloning of an antibody light chain, and a second expression cassette suitable for cloning of an antibody heavy chain.

The invention further provides the use of a DHODH-encoding nucleotide sequence as defined herein as a selection marker for isolating clones producing recombinant proteins. In one embodiment, said DHODH-encoding nucleotide sequence is used in combination with at least one DHODH inhibitor, in particular with teriflunomide, preferably at a concentration of teriflunomide of 25 to 200 µM, more preferably 50 to 100 µM, still more preferably 50 µM.

The invention also provides a cell line comprising an expression vector of the invention, described in more detail below.

Further provided is an expression system comprising an expression vector of the invention, and optionally a cell line according to the invention. The expression system may further comprise at least one selection agent which is a DHODH inhibitor as described herein. In one embodiment, the DHODH inhibitor is teriflunomide, preferably at a concentration of 25 to 200 µM, more preferably 50 to 100 µM, still more preferably 50 µM.

Thus, the invention provides an expression system which is a combination of (i) a eukaryotic cell line; and (ii) an expression vector suitable for production of a recombinant protein, wherein said vector comprises a sequence coding for a mammalian dihydroorotate synthetase (DHODH) (homologous or heterologous with respect to the eukaryotic cell line) and at least one expression cassette for expressing a recombinant protein, and (iii) a DHODH inhibitor. In one embodiment, the DHODH inhibitor is teriflunomide, preferably at a concentration of 25 to 200 µM, more preferably 50 to 100 µM, still more preferably 50 µM.

In specific embodiments, said eukaryotic cell line is a CHO or a human cell line. In a particular embodiment, when the eukaryotic cell line is a CHO cell line, the sequence coding for the DHODH comprised in the expression vector is not a hamster DHODH sequence.

When the expression system is used for producing a recombinant protein, the vector is introduced into the cell line (it may for example be stably or transiently transfected into the cell line). The present invention thus provides an expression system which is (i) a combination wherein the vector is present within the cell line, or (ii) a combination wherein the vector is isolated from the cell line.

The expression system according to the invention may for example be provided under the form of a kit, e.g. with one vial comprising the expression vector, and another vial comprising the cell line. The invention provides in general a kit comprising an expression vector as described herein, and optionally a cell line of the invention and/or a DHODH inhibitor. In one embodiment, the DHODH inhibitor is teriflunomide, preferably at a concentration of 25 to 200 µM, more preferably 50 to 100 µM, still more preferably 50 µM.

The invention also provides a method of producing a recombinant protein comprising the steps of: providing a cell line of the invention as defined herein; culturing said cell line obtained under conditions suitable for production of the recombinant protein; and isolating and/or purifying said recombinant protein. The method may further comprise the step of formulating said recombinant protein into a pharmaceutical composition.

Also provided is the use of an expression vector, a cell line, an expression system, or a kit according to the invention for producing a recombinant protein.

DETAILED DESCRIPTION OF THE INVENTION

Dihydroorotate Dehydrogenase

Figure 1A:
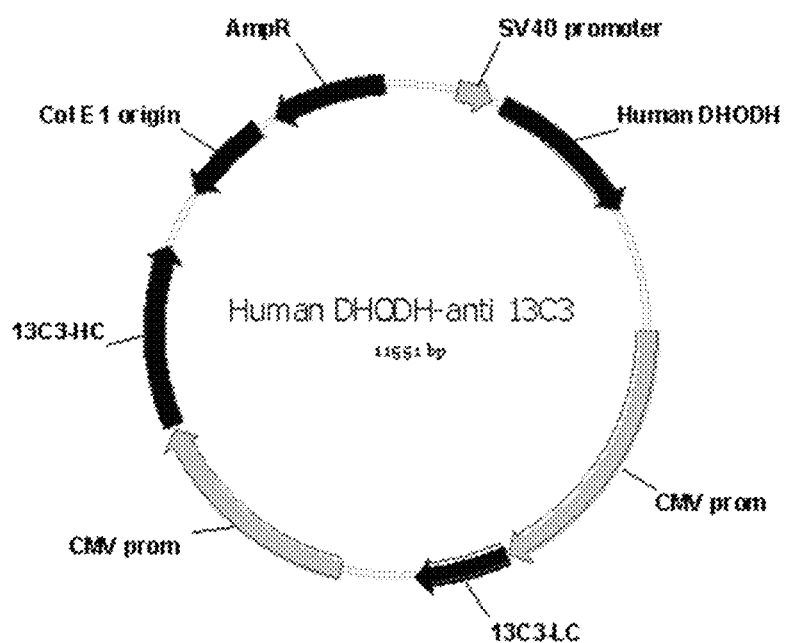
FIGS. 1A and 1B show in schematic form the vectors used in the Examples.

As used herein, the term "dihydroorotate dehydrogenase" or "DHODH"." refers to a polypeptide capable of catalyzing the conversion of dihydroorotate (4,5-dihydroorotic acid or 2,6-dioxo-1,3-diazinane-4-carboxylic acid) to orotate (orotic acid or 1,2,3,6-tetrahydro-2,6-dioxo-4-pyrimidinecarboxylic acid), as represented by the following reaction:

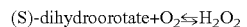

$$(S)\text{-dihydroorotate} + O_2 \leftrightharpoons H_2O_2$$

Such a polypeptide is classified under Enzyme Commission (EC) number 1.3.3.1. Polypeptides capable of catalyzing the above reaction exhibit "DHODH activity".

The above reaction is the fourth step in the de novo synthesis of uridine monophosphate (rUMP) required for the synthesis of DNA and RNA. Inhibition of DHODH thus has the effect of inhibiting DNA and RNA synthesis and hence inhibits cell proliferation.

The DHODH that is used in the present invention (further referred to as "DHODH of the invention") may comprise or consist of a sequence at least 90%, 91%; 92%; 93%, 94%, 95%, 95.5%, 96%, 96.5%, 97%, 97.5%, 98%, 98.5%, 99%, 99.5% or 100% identical to SEQ ID NO: 2 or SEQ ID NO: 4. It may also comprise or consist of a fragment of at least 100, 150, 200, 250, 300 or 350 consecutive amino acids of SEQ ID NO: 2 or SEQ ID NO: 4, provided the protein retains DHODH activity and its sensitivity to DHODH inhibitors.

In some embodiments, the DHODH according to the invention comprises or consists of a sequence at least 90%, 91%; 92%; 93%, 94%, 95%, 95.5%, 96%, 96.5%, 97%, 97.5%, 98%, 98.5%, 99%, 99.5% or 100% identical both to the sequence of SEQ ID NO: 2 and to the sequence of SEQ ID NO: 4.

In some embodiments, the DHODH according to the invention is a human DHODH, i.e., a DHODH of human origin. As used herein, the term "human DHODH" refers to a sequence comprising or consisting of SEQ ID NO: 4, as well as variants thereof exhibiting DHODH activity. Such variants may for example correspond to variants that occur naturally in human species (such as allelic variants or splice variants). Alternatively, such variants may correspond to variants obtained by genetic engineering. In one embodiment, such variants only differ from the sequence of SEQ ID NO: 4 by the presence of at most 25, 24, 23, 22, 21, 20, 19, 18, 17, 16, 15, 14, 13, 12, 11, 10, 9, 8, 7, 6, 5, 4, 3, 2 or 1 amino acid variations as compared to SEQ ID NO: 4 (said variations including substitutions, insertions and deletions).

In some embodiments, the DHODH is a hamster DHODH, i.e., a DHODH of hamster origin. The hamster DHODH may be, for example, Chinese hamster (*Cetulus griseus*) DHODH. As used herein, the term "Chinese hamster DHODH" refers to a sequence comprising or consisting of SEQ ID NO: 2, as well as variants thereof exhibiting DHODH activity. Such variants may for example correspond to variants that occur naturally in hamster species (such as allelic variants or splice variants). Alternatively, such variants may correspond to variants obtained by genetic engineering. In one embodiment, such variants only differ from the sequence of SEQ ID NO: 2 by the presence of at most 25, 24, 23, 22, 21, 20, 19, 18, 17, 16, 15, 14, 13, 12, 11, 10, 9, 8, 7, 6, 5, 4, 3, 2 or 1 amino acid variations as compared to SEQ ID NO: 2 (said variations including substitutions, insertions and deletions).

In another embodiment, the variant DHODH will have DHODH activity, optionally the same level of activity as the wild-type protein, or 50%, 60%, 70%, 80%, 90%, 100%, 110%, 120%, 130%, 140% or more of the level of activity as the wild-type protein.

In another embodiment, the variant DHODH will retain sensitivity to inhibitors of DHODH activity, for example teriflunomide.

In some embodiments, DHODH is sensitive to at least one DHODH inhibitor, in particular to teriflunomide. Inhibitors of DHODH include cinchoninic acid, brequinar (6-fluoro-2-(2'-fluoro-1,1'-biphenyl-4-yl)-3-methyl-4-quinoline carboxylic acid), naphthoquinone derivatives such as dichloroally lawsone, isoxazole derivatives such as leflunomide (5-methyl-N-[4-(trifluoromethyl) phenyl]-isoxazole-4-carboxamide) and its active metabolite teriflunomide ((2Z)-2-cyano-3-hydroxy-N-[4-(trifluoromethyl)phenyl]but-2-enamide), quinolone carboxylic acids, naphthoquinones, isoxazoles, phenoxyquinolines, redoxal and derivatives, lawsone, lapachol, atovaquone and (8-chloro-4-(2-chloro-4-fluoro-phenoxy)quinoline). An inhibitor of DHODH may be able to inhibit DHODH activity by at least 20, 30, 40, 50, 60, 70, 80, 90, 95, 99 or 100%. Said inhibitor may be used at a concentration of for example 50, 100, 200, 300, 400, 500, 600, 700, 800, 900 nM, 1, 10, 20, 50, 100, 200, 300, 400, 500, 600, 700, 800, 900 µM, 1 mM or more. In particular embodiments, the DHODH inhibitor is teriflunomide and it is used at a concentration of 25 and 200 µM, preferably 50 to 100 µM, more preferably 50 µM.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

Sequence identity may be determined over the full length of the variant sequence, the full length of the reference sequence, or both. For example, the percentage of identity may be calculated using a global alignment (i.e., the two sequences are compared over their entire length). Methods for comparing the identity and homology of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used when performing a global alignment. This needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Variants of a reference sequence may comprise mutations such as deletions, insertions and/or substitutions compared to the reference sequence. In case of substitutions, the substitution preferably corresponds to a conservative substitution as indicated in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

Vectors

The vector according to the invention is suitable for the production of a recombinant protein, and comprises a sequence encoding dihydroorotate dehydrogenase (DHODH). The vector is preferably a DNA vector.

The vector according to the invention comprises a sequence encoding such a DHODH according to the invention. The sequence encoding such a DHODH according to the invention may be the naturally-occurring nucleotide sequence. Alternatively, the triplet codons of the sequence encoding such a DHODH may be biased for expression in CHO cells. Software and algorithms for biasing sequence in order to obtain an optimal expression are known in the art and include, e.g., the algorithm described in Raab et al. (2010, Syst Synth Biol. 4:215-25). This algorithm not only provides the best available codons for expression, but also takes into account the GC content and the absence of non desired DNA motifs.

For instance, the sequence encoding the DHODH according to the invention may comprise or consist of a sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to the sequence of SEQ ID NO: 3 (i.e. a sequence encoding the human DHODH of SEQ ID NO: 4, which has been designed for optimal expression in CHO cells) and/or to the sequence of SEQ ID NO: 1 (i.e. a sequence encoding a hamster DHODH of SEQ ID NO: 2, which has been designed for optimal expression in CHO cells).

In one embodiment, the sequence encoding the DHODH according to the invention comprises or consists of a sequence of SEQ ID NO: 1 or SEQ ID NO: 2.

In the vector according to the invention, the sequence encoding the DHODH may be placed under the control of any promoter known to those skilled in the art.

For instance, the sequence encoding the DHODH may for example be placed under the control of a promoter suitable for driving expression of DHODH, for instance a Simian vacuolating virus 40 (SV40) promoter (e.g. the late or the early promoter of SV40), CMV promoter, Elongation Factor 1 promoter, GAPDH promoter, RPL37 promoter, Actin Promoter. An early SV40 promoter is for example described in Benoist and Chambon (1981, Nature. 290:304-10) and in Moreau et al. (1981, Nucleic Acids Res. 9:6047-68). In particular, said SV40 promoter is a full-length promoter. Said SV40 promoter may also have a replication origin containing a 72 bp repeat.

In some embodiments, said SV40 promoter is not an SV40 promoter in which positions 128 to 270 have been removed, i.e. said SV40 promoter is not the SV40 promoter described in Korean patent No. 10-0267720 and the *E. coli* transformant deposited to the Gene Bank, Institute of Bioengineering, KIST on 17 Dec. 1997 under the Deposition Number: KCTC 8860 P.

In other embodiments, the sequence encoding the DHODH according to the invention is not placed under the control of a SV40 promoter.

Vectors that are suitable for the production of recombinant proteins are known to those skilled in the art. Such vectors typically correspond to expression vectors that comprise an origin of replication and at least one expression cassette allowing the cloning and the expression of the recombinant protein for which production is desired. An expression cassette typically comprises a 5' untranslated region (comprising or consisting of a promoter, and optionally an enhancer sequence), one or more restriction sites allowing the cloning of a sequence encoding the recombinant protein, a 3' untranslated region (e.g. a polyA signal), and optionally one or more introns. The promoter sequence may correspond to any strong promoter well-known to the art, such as e.g. the human CMV promoter. Optionally, the vectors according to the invention comprise a prokaryotic origin of replication (e.g. a prokaryotic replicon such as ColE1 in *E. coli*) and at least a prokaryote-selective marker gene, also known as prokaryotic selectable marker, so that the vectors allows for replication in prokaryotic cells. The cells which replicate the vectors also express the prokaryote-selective marker gene, and therefore can be identified and selected. Prokaryote-selective marker genes are well known to the person skilled in the art. Examples of prokaryote-selective marker genes are for instance nucleic acid sequences encoding a protein conferring antibiotic resistance (e.g. a sequence encoding a protein conferring resistance to ampicillin, chloramphenicol, blasticidin or kanamycine). The vector according to the invention may for instance have the structure depicted on FIG. 1, which is explained in more detail in Example 1, wherein the sequences encoding the heavy chain and the light chain of 13C3 antibody or anti-CD38 antibody may be replaced with two other coding sequences (e.g. sequences encoding the heavy chain and the light chain of another antibody).

The recombinant protein may correspond to any protein that is of interest to those skilled in the art. As used herein, the term "protein" is meant to encompass peptides (i.e. amino acid chains of less than 50 amino acids), polypeptides (i.e. amino acid chains of at least 50 amino acids), monomeric proteins (i.e. proteins consisting of one amino acid chain) and multimeric proteins (i.e. proteins consisting of two or more amino acid chains, such as e.g. monoclonal antibodies).

The vector according to the invention typically comprises a number of expression cassettes that is identical to the number of different amino acid chains that constitute the protein (e.g. one expression cassette in case of a monomeric protein or homodimeric protein, two in the case of a heterodimeric protein or of a monoclonal antibody, etc.).

Alternatively, the DNA vector according to the invention may comprise only one expression cassette even when production of a heterodimeric protein or of a monoclonal antibody is desired. In such a case, the sequence(s) encoding the other amino acid chain(s) of the protein is (are) present on a separate expression vector, which is co-transfected with the vector according to the invention into the host cell line.

In one embodiment, the DNA vector according to the invention may be devoid of expression cassette. In such a case, the expression cassette(s) suitable for expression of the recombinant protein is (are) present on a separate vector, which is co-transfected with the vector according to the invention into the host cell line, in particular into the CHO cell line.

Thus, in some embodiments, the expression vector of the invention comprises:
  a sequence encoding DHODH, placed under the control of the early SV40 promoter;
  a first expression cassette, in which the sequence encoding the light chain of the antibody is placed under the control of the CMV promoter;
  a second expression cassette, in which the sequence encoding the heavy chain of the antibody is placed under the control of the CMV promoter;
  a prokaryotic origin of replication; and
  a selectable marker for use in prokaryotic cells, namely a sequence encoding a protein conferring resistance to ampicillin, placed under the control of its natural promoter.

Throughout the present specification, the term "recombinant protein" refers to any recombinant protein for which production is desired. It can for example correspond to a therapeutic and/or a prophylactic protein, i.e. a protein intended for use as a medicament (including vaccines). In a specific embodiment, the recombinant protein for which production is desired is not a DHODH. In another specific embodiment, the recombinant protein for which production is desired is an antibody, for instance a monoclonal antibody. In still another specific embodiment, the recombinant protein for which production is desired is an antigenic protein.

The term "antibody" is used herein in the broadest sense and specifically covers monoclonal antibodies (including full length monoclonal antibodies) of any isotype such as IgG, IgM, IgA, IgD, and IgE, polyclonal antibodies, multi-specific antibodies (including bispecific antibodies), antibody fragments (such as e.g. Fv, scFv, dsFv, Fab, Fab', or F(ab')2 fragments), and fusion proteins comprising an antibody fragment. An antibody reactive with a specific antigen can be generated by recombinant methods such as selection of libraries of recombinant antibodies in phage or similar vectors, or by immunizing an animal with the antigen or an antigen-encoding nucleic acid.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope (or a single group of epitopes in the case of multispecific monoclonal antibodies) and are therefore highly specific.

A typical monoclonal antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus (see Kabat et al., Sequences of Proteins of Immunological Interest, 5th edition, National Institute of Health, Bethesda, Md., 1991). The more highly conserved portions of the variable regions are called the "framework regions".

The monoclonal antibody may for example be a murine antibody, a chimeric antibody, a humanized antibody, or a fully human antibody.

When the recombinant protein for which production is desired is a monoclonal antibody, the vector according to the invention may comprise a first expression cassette suitable for cloning of the antibody light chain, and a second expression cassette suitable for cloning of the antibody heavy chain.

In a specific embodiment, said first and second expression cassettes each comprise the cytomegalovirus (CMV) promoter, for instance a CMV promoter from a human or a murine CMV. More specifically, said first and second expression cassettes may comprise:
- a CMV immediate early enhancer promoter (e.g. the one having the sequence described in Teschendorf et al., 2002, Anticancer Res. 22:3325-30); or
- a 1E2 promoter/enhancer region from mouse CMV (e.g. the one having the sequence described in Chatellard et al., 2007, Biotechnol Bioeng. 96:106-17); or
- a hCMV-MIE regulatory element (e.g. the one having the sequence described in WO 89/01036).

The term "antigenic protein" is used herein in the broadest sense and covers any protein capable of generating an immune response, either alone or in combination with an adjuvant. It may be intended for use either in a prophylactic vaccine or in a therapeutic vaccine. In a specific embodiment the antigenic protein is a vaccinal protein, i.e. a protein intended for use in a prophylactic vaccine.

The expression vector may either comprise at least one sequence encoding the recombinant protein of interest (e.g. one sequence encoding a monomeric protein, one sequence encoding an antibody chain, or two sequences, encoding an antibody light chain and an antibody heavy chain, respectively), or it may be empty (i.e. devoid of such a sequence encoding the recombinant protein of interest).

In one aspect, the invention is directed to the vector according to the invention per se. Such a vector is preferably intended for use in a mammalian cell line. However, it may also be used for expressing proteins in other eukaryotic cell lines such as yeast, fungal or insect.

Cell Lines

The invention provides a cell line comprising a vector according to the invention. In one embodiment, said cell line is transfected (stably or transiently transfected) with said vector. In another embodiment said cell line comprises said vector integrated in its genome.

The cell line is a eukaryotic cell line, e.g. a mammalian cell line such as a CHO cell line, a monkey cell line or a human cell line.

More specifically, the invention provides a cell line comprising a DNA expression vector, and wherein said vector comprises a nucleotide sequence encoding a mammalian DHODH (homologous or heterologous with respect to the eukaryotic cell line) and at least one expression cassette for expressing a recombinant protein.

CHO cell lines are commonly used for industrial protein production, and many CHO cell lines are known to those skilled in the art. For instance, such CHO cell lines include, strains which are publicly available from the American Type Culture Collection such as the CHO-K1 cell line (ATCC Number: CCL-61), the CHO-S cell line (marketed for instance by Invitrogen and Gibco), the CHO DP-12 cell line (ATCC Nos. CRL-12444 and 12445) and the CHO 1-15 cell line (ATCC Number CRL-9606). Another cell line suitable for industrial protein production is the CHO 9E4 cell line. The 9E4 cell line was established from a clone of the CHO-K1 cell line through a single cell cloning process. The CHO-K1 cell line was obtained by Puck in 1957 and has been deposited at the ATCC under number CCL-61.

In a specific embodiment, the cell line is a CHO cell line and the DHODH is of heterologous origin (i.e. DHODH is not a hamster DHODH).

Human cells such as HEK293 (ATCC Number CRL-1573), HKB11 (ATCC Number CRL-12568), PER-C6 (Crucell), HT1080 (ATCC Number CRL-121), Jurkat, Daudi, Raji and CAP (ATCC Number CRL-1098) cells may also be used for protein production, in order to obtain a native glycosylation pattern for recombinant human proteins.

In one embodiment, the cell line is capable of growing in serum-free medium (e.g. a chemically-defined medium) and/or in suspension. Such a cell line can easily be obtained by those skilled in the art by adapting the parent cell line to grow in serum-free medium and/or in suspension (e.g. through single cell cloning, through progressive adaptation and/or through a "starve and save" process). The cell line may either be a DHODH deficient cell line, or a cell line comprising an endogenous DHODH gene encoding an wild-type DHODH polypeptide.

Kits, Methods and Uses According to the Invention

The invention provides a kit comprising or consisting of all or part of an expression system according to the invention. The kit comprises a DHODH-encoding expression vector as described herein. In such a kit, the vector is preferably empty, since this allows the cloning of the protein of interest for those skilled in the art. In addition, the DNA vector is preferably isolated from the cell line in such a kit. The kit may further comprise a cell line as described herein, at least one selection agent such as at least one inhibitor of DHODH as described herein, media suitable for cultivation of the cell line, media suitable for transfection of the vector into the cell line, a packaging material and/or instructions for use of the expression system. In one embodiment, the DHODH inhibitor is teriflunomide, preferably at a concentration of 25 to 200 µM, more preferably 50 to 100 µM, still more preferably 50 µM.

The invention further provides the use of the expression system according to the invention, or of the vector according to the invention, or of the cell line according to the invention, or of the kit according to the invention, for producing a recombinant protein in vitro. In one embodiment, at least one DHODH inhibitor, in particular teriflunomide, is used to implement the use of the expression system according to the invention, of the vector according to the invention, of the cell line according to the invention, or of the kit according to the invention, for producing a recombinant protein in vitro. When teriflunomide is used, it is used preferably at a concentration of 25 to 200 µM, more preferably 50 to 100 µM, still more preferably 50 µM.

The invention further provides the use of the expression system according to the invention, or of the vector according to the invention, or of the cell line according to the invention, or of the kit according to the invention, for isolating a clone cell which produces high levels of a recombinant protein ("high producing clones") in vitro. In one embodiment, at least one DHODH inhibitor, in particular teriflunomide, is used to implement the use of the expression system according to the invention, of the vector according to the invention, of the cell line according to the invention, or of the kit according to the invention, for producing a recombinant protein in vitro. When teriflunomide is used, it is used preferably at a concentration of 25 to 200 μM, more preferably 50 to 100 μM, still more preferably 50 μM.

In the context of the invention, the term "high level of a recombinant protein" is intended to mean that in the culture medium the concentration of recombinant protein is of at least 0.05 g/l, preferably at least 0.1 g/l, still preferably at least 0.2 g/l, more preferably between 0.3 and 1 g/l. The concentration of recombinant protein can be determined by methods which are well known to the person skilled in the art, including in particular Enzyme-linked immunosorbent assay (ELISA), Western blot, a caliper technology and a range of concentration of the purified protein corresponding to the recombinant protein.

The invention further provides an in vitro method of producing a recombinant protein, said method comprising or consisting of the following steps:
 a) providing a cell line;
 b) transfecting said cell line with a vector according to the invention;
 c) culturing the transfected cell line obtained at step (b) under conditions suitable for production of the recombinant protein; and
 d) isolating and/or purifying said recombinant protein.

In a particular embodiment, step (c) of the above method is conducted in the presence of the DHODH inhibitor and comprises a sub-step consisting in selecting the transfected cells which are resistant to the DHODH inhibitor. In one implementation of this particular embodiment the DHODH inhibitor is teriflunomide. In another implementation of this specific embodiment recited above, step (c) is conducted in the presence of a concentration of teriflunomide comprises of 25 to 200 μM, preferably of 50 to 100 μM, more preferably 50 μM.

As immediately apparent to those skilled in the art, the above aspect relates to a expression system according to the invention wherein the DNA vector is isolated from the cell line at step (a).

The invention further provides an in vitro method of isolating a clone cell which produces high levels of a recombinant protein, said method comprising or consisting of the following steps:
 a) providing a cell line;
 b) transfecting said cell line with a vector according to the invention;
 c) culturing the transfected cell line obtained at step (b) under conditions suitable for production of the recombinant protein; and
 d) isolating a clone cell which produces high levels of a recombinant protein.

In a particular embodiment, step (c) of the above method is conducted in the presence of the DHODH inhibitor and comprises a sub-step consisting in selecting the transfected cells which are resistant to the DHODH inhibitor. In one implementation of this particular embodiment the DHODH inhibitor is teriflunomide. In another implementation of this specific embodiment recited above, step (c) is conducted in the presence of a concentration of teriflunomide comprises of 25 to 200 μM, preferably of 50 to 100 μM, more preferably 50 μM.

The invention further provides an in vitro method of producing a recombinant protein, said method comprising or consisting of the following steps:
 a) providing an expression system according to the invention;
 b) culturing the transfected cell line under conditions suitable for production of the recombinant protein; and
 c) isolating and/or purifying said recombinant protein.

In a specific embodiment, step (b) of the above method is conducted in the presence of the DHODH inhibitor and comprises a sub-step consisting in selecting the transfected cells which are resistant to the DHODH inhibitor. In one implementation of this specific embodiment the DHODH inhibitor is teriflunomide. In another implementation of this specific embodiment recited above, step (b) of the above method is conducted in the presence of a concentration of teriflunomide comprises of 25 to 200 μM, preferably of 50 to 100 μM, more preferably 50 μM.

The invention further provides an in vitro method of isolating a clone cell which produces high levels of a recombinant protein, said method comprising or consisting of the following steps:
 a) providing an expression system according to the invention;
 b) culturing the transfected cell line under conditions suitable for production of the recombinant protein; and
 c) isolating a clone cell which produces high levels of a recombinant protein.

In a specific embodiment, step (b) of the above method is conducted in the presence of the DHODH inhibitor and comprises a sub-step consisting in selecting the transfected cells which are resistant to the DHODH inhibitor. In one implementation of this specific embodiment the DHODH inhibitor is teriflunomide. In another implementation of this specific embodiment recited above, step (b) of the above method is conducted in the presence of a concentration of teriflunomide comprises of 25 to 200 μM, preferably of 50 to 100 μM, more preferably 50 μM.

As immediately apparent to those skilled in the art, the above aspect relates to an expression system according to the invention wherein the cell line comprises the DNA vector (e.g. the cell line has previously been transected with the DNA vector) at step (a).

The invention further provides an in vitro method of producing a recombinant protein, comprising or consisting of the following steps:
 a) providing a vector according to the invention, wherein said vector comprises at least one sequence encoding a recombinant protein;
 b) transfecting a cell line with said vector;
 c) culturing the transfected cell line obtained at step (b) under conditions suitable for production of the recombinant protein; and
 d) isolating and/or purifying said recombinant protein.

Conditions suitable for production of recombinant proteins are well-known to those skilled in the art. The protocols described in the Examples may for instance be used.

In a specific embodiment, at least one DHODH inhibitor such as leflunomide or teriflunomide is added when culturing the cell line according to the invention. In another specific embodiment, increasing concentrations of such inhibitor are added when culturing the cell line. This allows selecting clones in which the vector-derived DHODH gene (and thus the sequence encoding the recombinant protein) has been amplified. In one implementation of the specific embodiments recited above the DHODH inhibitor is teriflunomide. In another implementation of the specific embodiments recited above, 25 to 200 μM, preferably of 50 to 100 μM, more preferably 50 μM of teriflunomide is added when culturing the cell line according to the invention.

The above methods may further comprise the step of formulating the recombinant protein into a pharmaceutical composition.

The invention further provides an in vitro method of isolating a clone cell which produces high levels of a recombinant protein, comprising or consisting of the following steps:
  a) providing a vector according to the invention, wherein said vector comprises at least one sequence encoding a recombinant protein;
  b) transfecting a cell line with said vector;
  c) culturing the transfected cell line obtained at step (b) under conditions suitable for production of the recombinant protein; and
  d) isolating a clone cell which produces high levels of a recombinant protein.

In a specific embodiment, at least one DHODH inhibitor such as leflunomide or teriflunomide is added when culturing the cell line according to the invention (i.e. step (c)). In another specific embodiment, increasing concentrations of such inhibitor are added when culturing the cell line. This allows selecting clones in which the vector-derived DHODH gene (and thus the sequence encoding the recombinant protein) has been amplified. In one implementation of the specific embodiments recited above the DHODH inhibitor is teriflunomide. In another implementation of the specific embodiments recited above, 25 to 200 µM, preferably of 50 to 100 µM, more preferably 50 µM of teriflunomide is added in step (c).

The invention further provides a method for co-amplifying a recombinant DNA sequence which encodes a recombinant protein, comprising or consisting of the following steps:
  a) providing a vector according to the invention, wherein said vector comprises a sequence which encodes said recombinant protein;
  b) providing a cell line;
  c) transfecting said cell line with said vector; and
  d) culturing said transfected cell line under conditions which allow transformants containing an amplified number of copies of a vector-derived sequence which encodes DHODH to be selected, wherein said transformants also contain an amplified number of copies of the sequence which encodes the complete amino acid sequence of the recombinant protein.

In a specific embodiment, step (d) of the above method may comprise culturing the transfected cell line in medium containing a DHODH inhibitor and selecting for transformant cells which are resistant the DHODH inhibitor, in particular to progressively increased level of the DHODH inhibitor. In one implementation of the specific embodiment above the DHODH inhibitor is teriflunomide. In another implementation of the specific embodiment recited above the DHODH inhibitor is teriflunomide and it is used at a concentration of 25 to 200 µM, preferably 50 to 100 µM, more preferably 50 µM.

The invention further provides an in vitro method of isolating a clone cell which produces high levels of a recombinant protein, comprising or consisting of the following steps:
  a) providing a vector according to the invention, wherein said vector comprises a sequence which encodes said recombinant protein;
  b) providing a cell line;
  c) transfecting said cell line with said vector; and
  d) culturing said transfected cell line under conditions which allow transformants containing an amplified number of copies of a vector-derived sequence which encodes DHODH to be selected, wherein said transformants also contain an amplified number of copies of the sequence which encodes the complete amino acid sequence of the recombinant protein;
  e) isolating from the transfected cells of step (d) a clone cell which produces high levels of a recombinant protein.

In a specific embodiment, step (d) of the above method may comprise culturing the transfected cell line in medium containing a DHODH inhibitor and selecting for transformant cells which are resistant the DHODH inhibitor, in particular to progressively increased level of the DHODH inhibitor. In one implementation of the specific embodiment above the DHODH inhibitor is teriflunomide. In another implementation of the specific embodiment recited above the DHODH inhibitor is teriflunomide and it is used at a concentration of 25 to 200 µM, preferably 50 to 100 µM, more preferably 50 µM.

The invention further provides a method for using a DNA vector as a dominant selectable marker in a cotransformation process, wherein said method comprises or consists of the following steps:
  a) providing a vector according to the invention, wherein said vector comprises a sequence which encodes a recombinant protein;
  b) providing a cell line;
  c) transfecting said cell line with said vector; and
  d) selecting transformant cells which are resistant to DHODH inhibitor(s), whereby transformant cells are selected in which a vector-derived recombinant DNA sequence which encodes DHODH serves as a dominant selectable and co-amplifiable marker.

In a specific embodiment of the above method, the selected transformant cells are resistant to the DHODH inhibitor teriflunomide. In another embodiment of the above method, the selected transformant cells are resistant to a concentration of 25 to 200 µM, preferably of 50 to 100 µM, more preferably 50 µM of teriflunomide.

Throughout the specification, terms such as 'comprises', 'comprised', 'comprising' and can have the meaning attributed to them in most patent jurisdictions, preferably in the jurisdiction in question; e.g. they can mean 'includes', 'included', 'including', etc. Terms such as 'consisting of' 'consisting essentially of' and 'consists essentially of have the meaning ascribed to them in most patent jurisdictions, preferably in the jurisdiction in question; e.g., they imply the exclusion of all, most or all but a negligible amount of other elements, they allow for elements not explicitly recited, but exclude elements that are found in the prior art or that affect a basic or novel characteristic of the invention.

Several documents are cited throughout the text of this specification. Each of the documents cited herein (including any journal article or abstract, published or unpublished patent application, issued patent, manufacturer's specifications, instructions, etc.) are hereby incorporated by reference. However, there is no admission that any document cited herein is indeed prior art in respect of the present invention.

The invention will further be described by reference to the following drawings and examples, which are illustrative only, and are not intended to limit the present invention. The invention is defined by the claims, which should be interpreted with the help of the description and the drawings.

BRIEF DESCRIPTION OF THE SEQUENCES

SEQ ID NO: 1 shows a cDNA sequence encoding DHODH of Chinese hamster (*Cricetulus griseus*) origin.

SEQ ID NO: 2 shows the amino acid sequence of DHODH of Chinese hamster origin.

SEQ ID NO: 3 shows a cDNA sequence encoding DHODH of human origin.

SEQ ID NO: 4 the amino acid sequence of DHODH of human origin

EXAMPLES

Example 1: Creation of Expression Vectors Comprising DHODH Marker

The inventors aimed at developing new vectors for expression and production of recombinant proteins in eukaryotic cell lines. Two sets of vectors for antibody expression were designed, incorporating respectively human and Chinese hamster DHODH as selectable markers.

The first set of vectors comprised two cDNAs encoding a humanized version of the 13C3 antibody (one cDNA encoding the 13C3 heavy chain and another cDNA encoding the 13C3 light chain, respectively, the combination of said chains forming the humanized 13C3 antibody). The murine 13C3 antibody is an antibody that specifically binds to the protofibrillar form of the human β-amyloid protein, as described in WO 2009/065054. As further used herein, the term "13C3" refers to the humanized version of the murine 13C3 antibody.

The second set of vectors comprised two cDNAs encoding an anti-CD38 antibody (one cDNA encoding the heavy chain and another cDNA encoding the light chain, respectively, the combination of said chains forming the anti-CD38 antibody).

Figure 1B:
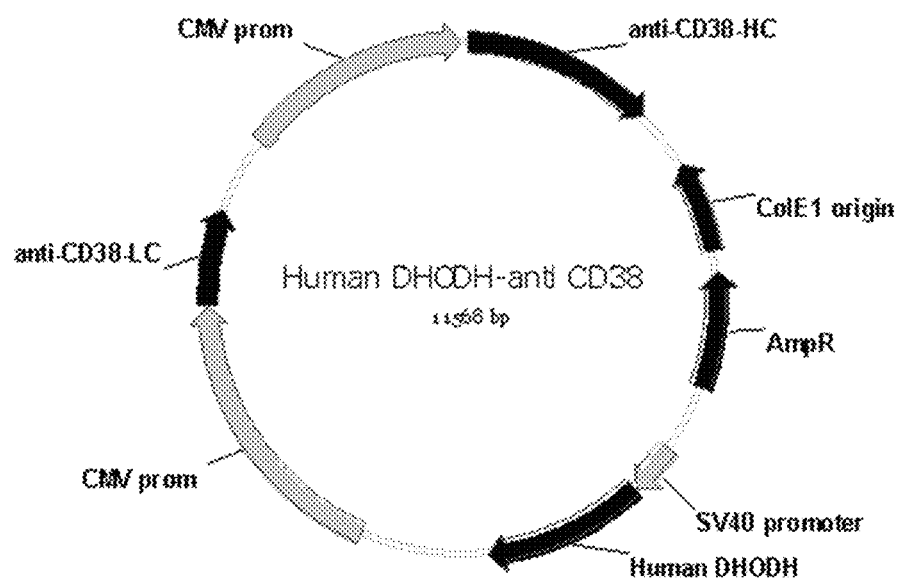
Figure 2A:
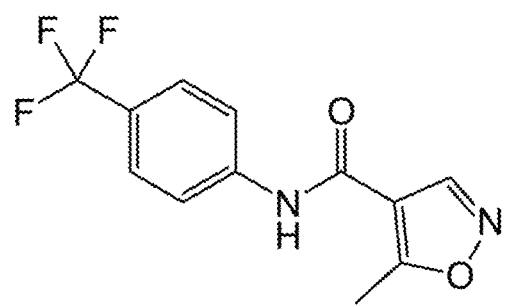
FIGS. 2A and 2B show structure of leflunomide (FIG. 2A) and its metabolite teriflunomide (FIG. 2B).
Figure 2B:
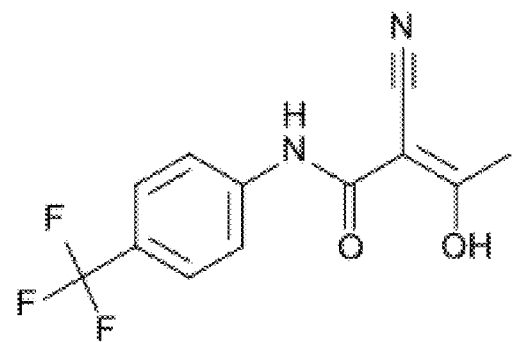

The vectors are schematically represented in FIG. 1. These vectors comprise:
- a sequence encoding DHODH, placed under the control of the early SV40 promoter;
- a first expression cassette, in which the sequence encoding the light chain of the antibody is placed under the control of the CMV promoter;
- a second expression cassette, in which the sequence encoding the heavy chain of the antibody is placed under the control of the CMV promoter;
- a prokaryotic origin of replication; and
- a selectable marker for use in prokaryotic cells, namely a sequence encoding a protein conferring resistance to ampicillin, placed under the control of its natural promoter.

More specifically, the sequence encoding DHODH is placed under the control of the SV40 promoter, including the SV40 enhancer. Such an SV40 early promoter contains the SV40 72-bp tandem repeat enhancers linked to the 21-bp non tandem repeats, and the SV40 early leader protein sequence excluding any coding sequence. The use of this region as a strong promoter was described by Benoist and Chambon (1981, Nature. 290:304-10) and in Moreau et al. (1981, Nucleic Acids Res. 9:6047-68). It is classically used as a promoter for expression of selection markers in mammalian cells. In the seven pBH3694 to pBH3700 vectors, the natural HindIII restriction site that was disrupted, and unique restriction sites (SalI and XmaI) were added at the 5' and the 3' end of the promoter region, in such a way as to allow an easy swapping of the different DHODH cDNAs.

In each set of vectors, sequences encoding DHODH having different origins were cloned into the vectors.

More specifically, cDNAs coding respectively for DHODH from Chinese hamster (*Cricetulus griseus*) and human (*Homo sapiens*) were generated using the naturally-occurring (wild-type) amino acid sequences available in public databases. Starting from these sequences, the proteins were back-translated using a matrix of the most frequent codons used in CHO cells. Thereafter, the cDNAs were modified to contain proper cloning sites and the nucleotide sequences were optimized. Of note, while the nucleotide sequences were optimized for CHO expression, the amino acid sequence of encoded proteins remains identical to that of the naturally-encoded proteins.

More specifically, the naturally-occurring coding sequences for the different DHODH were taken as a starting point for. The human DHODH amino acid sequence corresponds to the one that is shown in NCBI Reference Sequence: NP_001352.2 (SEQ ID NO: 4). The Chinese hamster DHODH amino acid sequence corresponds to the one that is shown in NCBI Reference Sequence: XP_007634457.1 (SEQ ID NO: 2). Starting from the naturally-occurring cDNA sequences, the triplet codons of the sequence encoding such a DHODH was biased for expression in CHO cells using a software developed by Wagner and coworkers, which is based on the algorithm described in Raab et al. (2010, Syst Synth Biol. 4:215-25). This technique not only provides the best available codons for expression, but also takes into account the GC content and the absence of undesirable DNA motifs.

The obtained cDNAs were cloned into the backbone bearing the expression cassettes for 13C3 and anti-CD38 antibody, thereby yielding the vectors represented in FIG. 1.

The name of these vectors as well as the origin and sequence of the encoded DHODH is shown in the table below.

| Name | DHODH origin | Antibody | DHODH amino acid sequence | DHODH nucleotide sequence |
|---|---|---|---|---|
| pBH4939 | Hamster | anti-13C3 | SEQ ID NO: 2 | SEQ ID NO: 1 |
| pBH4940 | Hamster | anti-CD38 | SEQ ID NO: 2 | SEQ ID NO: 1 |
| pBH4952 | Human | anti-13C3 | SEQ ID NO: 4 | SEQ ID NO: 3 |
| pBH4967 | Human | anti-CD38 | SEQ ID NO: 4 | SEQ ID NO: 3 |

Example 2: Use of Vectors in CHO Expression System with Leflunomide and Teriflunomide as Selection Agent Preliminary experiments performed using CHO 9E4 cells indicated that leflunomide could be used as a selection agent. Briefly, the preliminary experiments showed that culturing CHO 9E4 cells with leflunomide did not kill the cells but inhibited growth at 50 and 100 µM. CHO 9E4 cells were transfected with plasmids bearing the cDNA encoding hamster DHODH and the genetic material for production of 13C3 antibodies and cultured in 96-well plates with 40 leflunomide. This obtained 27 wells with growing cells. Of these 27, 4 produced low but significant amount 13C3 antibody. However production was unstable and the efficiency was low below 0.1%. These experiments served as proof of principle that DHODH can be used as a selectable marker for recombinant protein production, so further experiments were performed.

The CHO 9E4 cell line was transfected with two different plasmids bearing the cDNA encoding human DHODH cDNA and the genetic material for production of anti CD38 or 13C3 antibodies (vectors pBH4952 and pBH4967). As a control vector for selection, the plasmid bearing a cDNA encoding human GS instead of DHODH (pBH3695) was transfected using into CHO 9E4 cell lines. The genetic material was transfected using standard electroporation techniques.

Twenty four hours post transfection, the selection process was started. For both the human and hamster DHODH, the cells were diluted in CD-CHO medium containing either 50 µM or 100 µM leflunomide or teriflunomide. The control vector was equally transfected and submitted to the same selection process.

In each case, 480 wells were seeded with 2000 cells/well. For the control vector, no growth was observed in any of the wells at both 50 and 100 µM teriflunomide even after 25 days.

Selection with leflunomide at both 50 and 100 µM was ineffective: in the presence of DHODH from human or hamster origin after 20 days, all the wells were displaying growing clones. All the supernatants corresponding to the 480 wells were tested for their capacity to produce antibodies, and none of the supernatants showed detectable amount of antibodies, confirming that leflunomide is difficult to use for this kind of experiments.

In the teriflunomide-selected transfection, growing cells appeared two weeks later in about of 8-10% of the wells for cells transfected with vector bearing the cDNA encoding human DHODH and the genetic material for production of anti-CD38, as well as for cells transfected with vector bearing the cDNA encoding human DHODH cDNA and the genetic material for production of anti-13C3 antibodies (vectors pBH4967 and pBH4952, respectively). A proportion of the wells produced antibody, some at over 10 µg/ml, as shown in Tables 1 and 2. In contrast, no growth was observed in any of the wells comprising cells transfected with vector bearing the cDNA encoding hamster DHODH and the genetic material for production of anti-CD38 or anti-13C3 antibodies (vectors pBH4940 and pBH4939, respectively).

TABLE 1

Results with 13C3 antibodies. Occupied wells show growing clones after 15 to 20 days.

| Teriflunomide 50 µM (13C3) | Number of wells |
|---|---|
| Tested | 480 |
| Occupied | 38 |
| % of Occupied | 8 |
| % of Producers | 3 |
| Antibody: Less than 10 µg/ml | 24 |
| Antibody: More than 10 µg/ml | 14 |

TABLE 2

Results with anti CD38 antibodies. Occupied wells show growing clones after 15 to 20 days.

| Teriflunomide 50 µM (anti-CD38) | Number of wells |
|---|---|
| Tested | 480 |
| Occupied | 48 |
| % of Occupied | 10 |
| % of Producers | 4 |
| Antibody: Less than 10 µg/ml | 29 |
| Antibody: More than 10 µg/ml | 19 |

Overall, in the case of 13C3, 14 wells out of 480 wells contained clones producing more than 10 µg/ml antibody, while for anti-CD38, 29 wells over 480 wells contained clones producing more than 10 µg/ml antibody. This efficiency was comparable with the standard selection marker human GS cDNA and the companion GS enzyme inhibitor methionine sulfoximine (MSX), where the percentage of occupied wells ranges from 1 to 10%. A typical result of such an experiment is given in Table 3.

TABLE 3

Results with 13C3 antibodies using GS/MSX expression system. Occupied wells show growing clones after 15 to 20 days.

| MSX 25 µM (13C3) | Number of wells |
|---|---|
| Tested | 960 |
| Occupied | 46 |

Example 3: Productivity Assessment Using Teriflunomide as Selection Agent

In order to measure the quantity of produced antibodies in more depth, the most promising clones were amplified and evaluated for productivities in a protocol mimicking bioreactor conditions.

Cells from wells producing the highest level of antibodies in Example 1 were chosen for further amplification. Each well contained 2000 cells at the beginning of the experiment, therefore, each well does not contain a clone per se. Each well cell is here referred to as a semi-clone. 14 wells corresponding to semi-clones producing 13C3 antibodies and 19 wells corresponding to semi-clones producing anti-CD38 antibodies were grown in suitable conditions.

As a positive control, 5 semi-clones corresponding to the MSX/GS expression system were amplified.

All the amplification experiments were performed in CD-CHO medium (Life Technologies) containing 50 µM teriflunomide or 25 µM MSX, respectively for human DHODH or human GS selection, at 37° C. with 5% $CO_2$ and 80% humidity.

The 96 well growing cells of each antibody producing were transferred into 1 ml medium in 24 well plates. After 3 days of growth, the 1 ml cell suspension was transferred into a 25 $cm^3$ flask containing 4 ml of fresh medium and the cells were grown with agitation for another 3 days. After 3 days of incubation, 5 ml of fresh medium were added. After numbering the cell suspension, another culture was seeded at $0.3 \times 10^6$ cells per ml and grown for another 3 days. Following this growth, a final culture was started for antibody production seeded at $0.3 \times 10^6$ cells per ml in CD-CHO medium+30% of Feed B.

The cell suspension was incubated for 13 days and samples were taken at 10 and 13 days incubation for evaluation of the antibody concentration.

Figure 3:
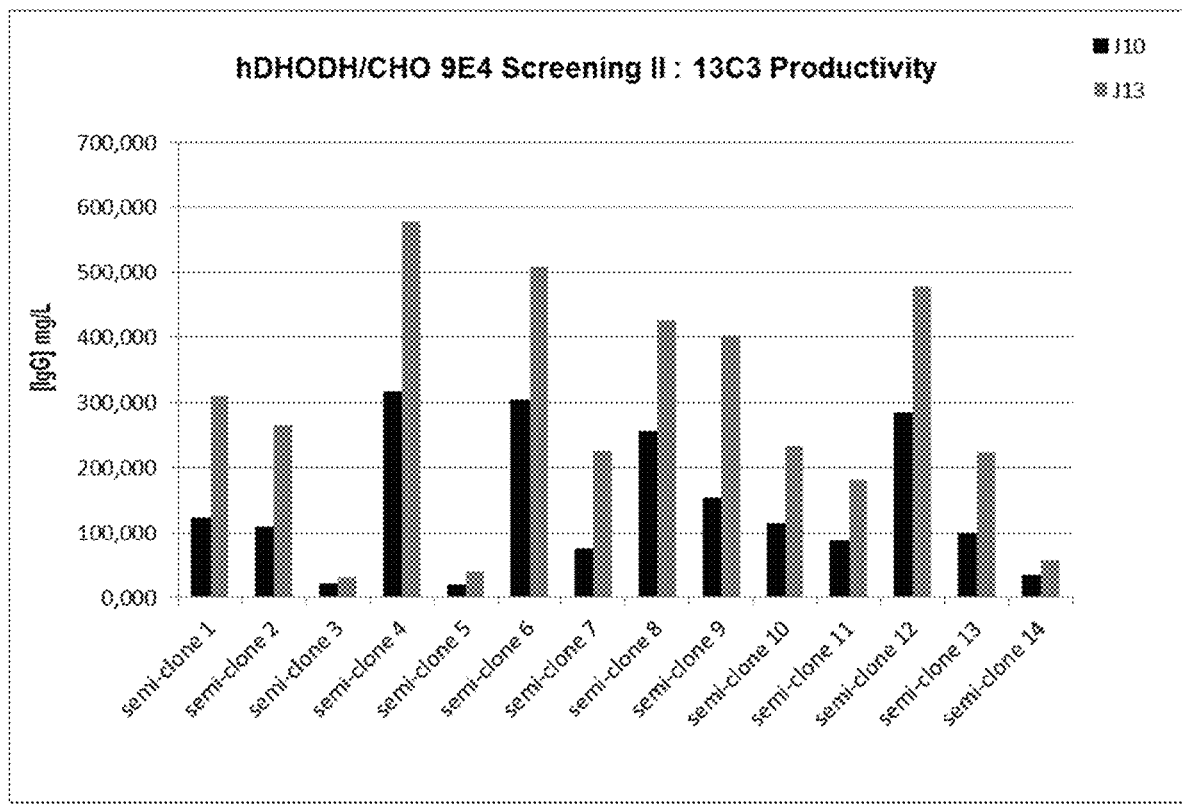
FIG. 3 shows the productivities achieved by 14 semi-clones obtained during production of anti-13C3 in CHO 9E4 cells using human DHODH as a selection marker.

FIG. 3 shows productivity of the 14 DHODH/13C3 semi-clones at Day 10 and Day 13 in the presence of 50 µM teriflunomide.

Figure 4:
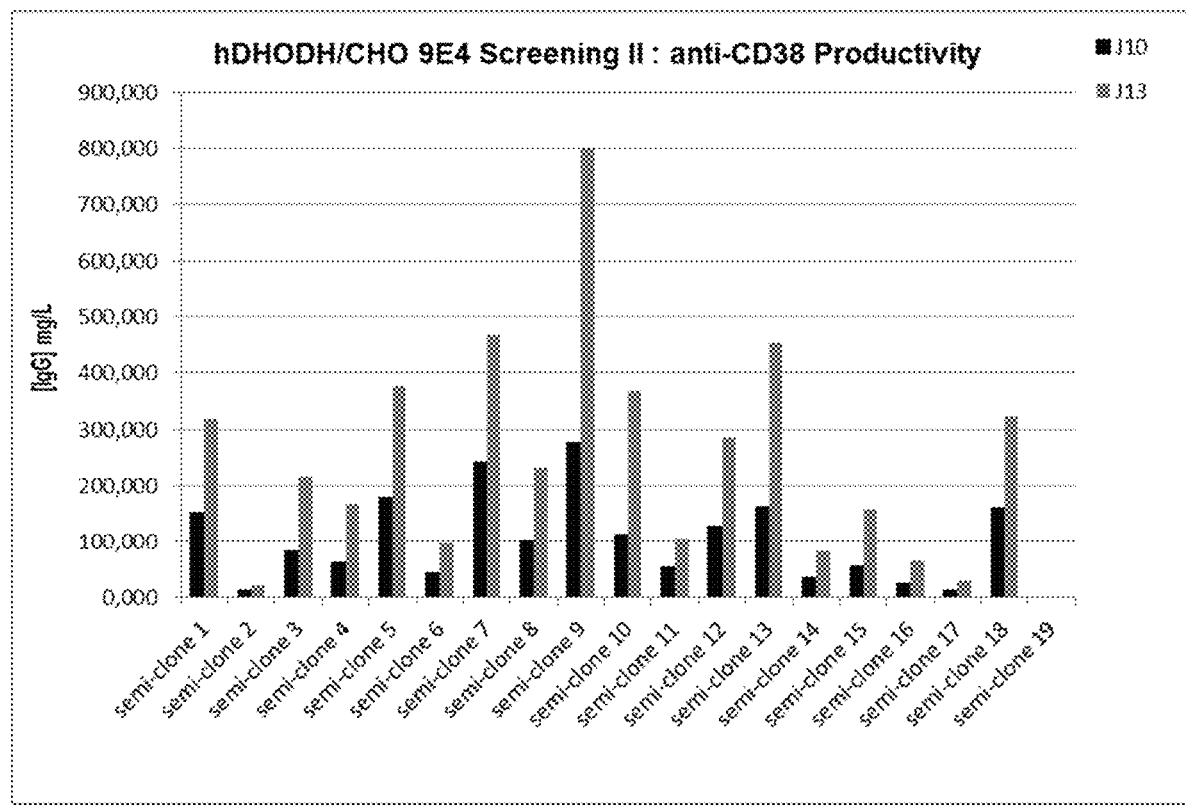
FIG. 4 shows the productivities achieved by 19 semi-clones obtained during production of anti-CD38 in CHO 9E4 cells using human DHODH as a selection marker).

FIG. 4 shows productivity of the 19 DHODH/anti-CD38 semi-clones at Day 10 and Day 13 in the presence of 50 µM teriflunomide.

Figure 5:
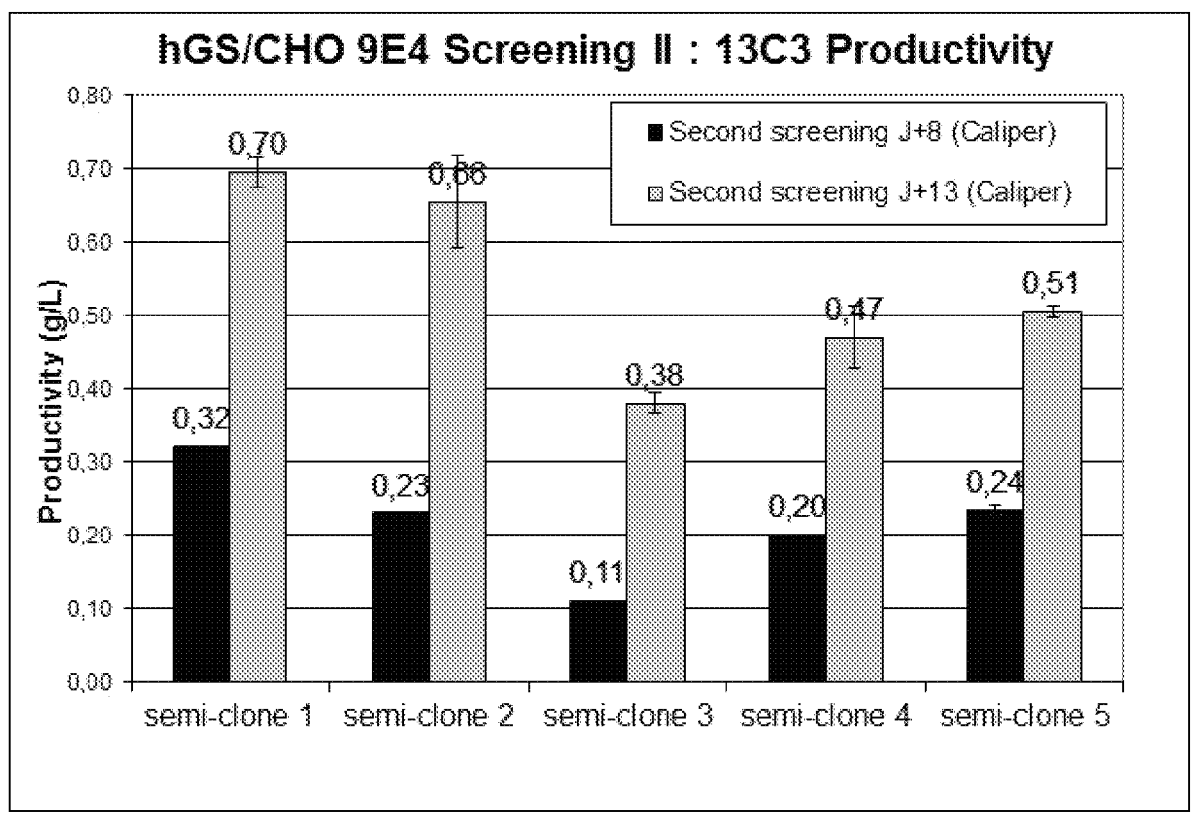
FIG. 5 shows the productivities achieved by 5 semi-clones obtained during production of anti-13C3 in CHO 9E4 cells using human GS as a selection marker.

Overall, the achieved productivities (0.5 to 0.8 g/l at day 13) and frequencies (about 3 to 10% of the 96 well productive semi-clones) were in the same range as the reference human GS in CHO 9E4 cells (see Table 3) or hamster GS in CHO K1SV cells. This can be seen from FIG. 5, which shows productivity of GS/13C3 CHO 9E4 semi-clones at days 8 and 13 in the presence of 25 µM MSX.

Example 4: Transient Transfection of CHO Cells Using the Reference GS Vector and the DHODH Based Vector

Experiment A: The 13C3 Antibody was Used to Measure Transfection Efficiency of DHODH Selection Marker Bearing Vectors To do so, vectors were prepared according to the specification of Maxcyte e.g. low endotoxin, ratio 260 nm/280 mn close to 2, concentration at 5 mg/ml. CHO-9E4 cells were electroporated using high efficiency electroporation protocol developed by Maxcyte on the Maxcyte STX® apparatus in quadruplicate with a control vector bearing a cDNA encoding human GS instead of DHODH, namely the plasmid pBH3695, and with a DHODH cDNA bearing vector namely pBH4952. Cells were split at $1 \times 10^6$ 24 h before transfection. For each transfection condition, $80 \times 10^6$ cells were centrifuged 10 min at 300 g. The pellet was resuspended with 200 μl Hyclone buffer (Maxcyte). DNA was added at 0.3 μg/μl and the mix (cells, buffer and DNA) was transferred into a 400 μl Maxcyte electroporation cassette. The processing assembly used was the OC-400 specific to 400 μl cassette, and the optimized program for HEK-293FS was selected. For the recovery phase, transfected cells were transferred in a 125 ml flask and incubated at 37° C. 40 min, without agitation. 20 ml pre-warmed Freestyle medium (Invitrogen) was added and cells were grown during 24 h at 37° C., 5% $CO_2$, 80% humidity and 110 rpm agitation. The cell growth was stopped by addition of sodium butyrate 1M (Merck) to reach 1 mM final concentration. Culture cells were maintained at 32° C. for 10 days and feed with 3.6% of a special producing feed (2.5% EfficientFeedA (Invitrogen), 0.5% Yeastcolate (Invitrogen), 2 g/L glucose (Sigma) and 0.25 mM GlutaMA (Invitrogen)) during 13 days.

The concentration of antibodies produced by the transiently transfected cells was measured, 7, 10, 11, 12 and 13 days after transfection, using the caliper technology and a range of concentration of the human purified antibody. These concentrations are displayed in Table 4.

TABLE 4

Concentration of 13C3 antibody (given in mg/L) produced by the transiently transfected cell lines.

| Vector | Selection marker | Antibody concentration at day D after transfection | | | | |
|--------|------------------|------|------|------|------|------|
|        |                  | D 7  | D 10 | D 11 | D 12 | D 13 |
| BH4952 | DHODH | 68.6 | 73.3 | 72.2 | 73.0 | 67.8 |
| BH3695 | GS    | 68.7 | 68.2 | 69.6 | 68.1 | 66.6 |

Experiment B

This experiment mainly aimed to (i) compare the production of 13C3 antibody of cells transiently transfected with different vectors (i.e. vector pBH3695 that encodes human GS as a selection marker and vector pBH4952 that encodes human DHODH as a selection marker), and (ii) compare the production of two different antibodies (i.e. 13C3 and anti-CD38 antibodies) using vector pBH4952 and pBH4967.

The experimental procedure used is the same as that disclosed above for experiment A. However, in experiment B two different CHO cell lines were tested (i.e. CHO 9E4 and CHO 30D12 (a cell line in which the gene encoding glutamine synthetase has been knocked out)) and the concentration of antibodies produced by the transfected cells was measured at 20 days. Further, three alternative processes of purification of vector pBH4952 (processes using a classic Qiagen column, a HiSpeed column—marketed by Qiagen—, and column of Macherey-Nagel, respectively) were tested to investigate the potential effect of the purification process on the final production of antibodies.

As it is apparent from Table 5 below that summarizes the results of this experiment, whatever the purification protocol used to purify the vector, the amounts of produced antibodies are similar. Also, the production of antibodies is similar in CHO 9E4 and CHO 30D12. Besides, since the concentrations of 13C3 and anti-CD38 antibodies produced by cells transfected with vectors expressing DHODH as a selection marker are similar (see data relating to vectors pBH4952 and pBH4967), it can be concluded that the antibody production does not depend upon the nature of the antibody.

Taken together, the above-results clearly show that DHODH can be used as a selection marker in an expression system and that such a system of expression is as least as effective as one using the selection marker GS.

| | Limit of detection ≥5 mg/L | | ProtA Mean Ab y = 52.459x | |
|---|---|---|---|---|
| Cell type | Sample | EP Protocol | Area (Blank substracted) | C (mg/L) |
| CHO 9E4 D 20 | pBH3695 Macherey 2.5 L | Transient/ Feed as described by MaxCyte | 15 738 | 238.1 |
| | pBH3695 Macherey 5 L | | 16 251 | 245.9 |
| | pBH3695 Qiagen 2.5 L | | 12 651 | 191.4 |
| | pBH3695 Qiagen 5 L | | 14 329 | 216.8 |
| | pBH3695 HiSpeed 2.5 L | | 17 522 | 265.1 |
| | pBH3695 HiSpeed 5 L | | 17 756 | 268.6 |
| | pBH4952 human DHODH 13C3 | | 15 680 | 237.2 |
| | pBH4967 human DHODH anti CD38 | | 16 005 | 242.1 |
| CHO 30 D 12 (KO GS) D 20 | pBH3695 Macherey 2.5 L | Transient/ Feed as described by MaxCyte | 16 638 | 251.7 |
| | pBH3695 Macherey 5 L | | 17 052 | 258 |
| | pBH3695 Qiagen 2.5 L | | 18 383 | 278.1 |
| | pBH3695 Qiagen 5 L | | 12 526 | 189.5 |
| | pBH3695 HiSpeed 2.5 L | | 15 932 | 241 |
| | pBH3695 HiSpeed 5 L | | 16 102 | 243.6 |
| | pBH4952 human DHODH 13C3 | | 15 660 | 236.9 |
| | pBH4967 human DHODH anti CD38 | | 11 427 | 172.9 |

In conclusion these results show that the vector of the invention can be used either in transient transfection or in stable transfection. It has capacities to produce recombinant antibodies with the same efficiency as the reference vector in both transfection technologies.

The invention claimed is:

1. An expression system comprising
   (a) an expression vector comprising a nucleotide sequence encoding a mammalian dihydroorotate dehydrogenase (DHODH) and at least one expression cassette for expressing a recombinant protein, wherein the DHODH comprises the nucleotide sequence of SEQ ID NO: 1 or a nucleotide sequence encoding an amino acid sequence that is at least 90% identical to the amino acid sequence of SEQ ID NO: 2, wherein the DHODH is inhibited by a DHODH inhibitor, and wherein the DHODH inhibitor is teriflunomide; and
   (b) at least one DHODH inhibitor, wherein the at least one DHODH inhibitor is teriflunomide.

2. A cell line comprising the expression system according to claim 1.

3. An in vitro method of producing a recombinant protein comprising:
   (a) culturing the cell line according to claim 2 under conditions suitable for production of the recombinant protein, wherein the cell line is cultured in the presence of a DHODH inhibitor, and wherein the DHODH inhibitor is teriflunomide; and
   (b) isolating and/or purifying the recombinant protein.

4. The method according to claim 3 further comprising formulating the recombinant protein into a pharmaceutical composition.

5. A method of using the expression system according to claim 1 for producing a recombinant protein comprising:
   (a) providing a cell line comprising the expression system according to claim 1;
   (b) culturing the cell line of (a) under conditions suitable for production of the recombinant protein, wherein the cell line is cultured in the presence of a DHODH inhibitor, and wherein the DHODH inhibitor is teriflunomide; and
   (c) isolating and/or purifying the recombinant protein.

* * * * *